(12) United States Patent
Lo

(10) Patent No.: US 6,488,657 B1
(45) Date of Patent: Dec. 3, 2002

(54) NEEDLE HOLDER POSITIONING STRUCTURE FOR SAFETY HYPODERMIC SYRINGE

(75) Inventor: Cheng-Chi Lo, Yungho (TW)

(73) Assignee: M.K. Meditech Co., Ltd., Taoyuan (TW)

( * ) Notice: Subject to any disclaimer, the term of this patent is extended or adjusted under 35 U.S.C. 154(b) by 0 days.

(21) Appl. No.: 09/993,572

(22) Filed: Nov. 27, 2001

(30) Foreign Application Priority Data

Sep. 21, 2001 (TW) ..................................... 90216217 U

(51) Int. Cl.7 ................................................ A61M 5/00
(52) U.S. Cl. ...................................... 604/110; 604/195
(58) Field of Search ................................ 604/110, 187, 604/181, 192, 195, 197–198, 218, 263, 240–242; 128/919

(56) References Cited

U.S. PATENT DOCUMENTS

| | | | | |
|---|---|---|---|---|
| 4,710,170 A | * | 12/1987 | Haber et al. ................. 604/110 |
| 4,883,471 A | * | 11/1989 | Braginetz et al. ............ 604/195 |
| 4,950,241 A | * | 8/1990 | Ranford ....................... 604/110 |
| 5,030,208 A | * | 7/1991 | Novacek et al. ............. 604/110 |
| 5,205,824 A | * | 4/1993 | Mazur ......................... 604/110 |
| 5,634,903 A | * | 6/1997 | Kurose et al. .............. 604/110 |
| 5,693,023 A | * | 12/1997 | Adams ........................ 604/110 |
| 5,820,605 A | * | 10/1998 | Zdeb et al. ................. 604/110 |
| 6,193,687 B1 | * | 2/2001 | Lo .............................. 604/110 |

* cited by examiner

Primary Examiner—Manuel Mendez
Assistant Examiner—Michael M Thompson
(74) Attorney, Agent, or Firm—Bacon & Thomas, PLLC

(57) ABSTRACT

A needle holder positioning structure for safety hypodermic syringe is disclosed, which includes a barrel, a needle holder with a sleeve, and a locating ring. The sleeve of the needle holder said sleeve has a front engagement section press-fitted into the inside of a front small inner diameter section of the barrel and a springy rear expansion section, the springy rear expansion section being expanded and positioned in between a shoulder and an inside flange in the barrel when a plunger inserted into the barrel to push the locating ring forwards and to force a front neck of the locating ring into a backwardly extended annular coupling chamber in the sleeve of the needle holder.

10 Claims, 7 Drawing Sheets

NEEDLE HOLDER POSITIONING STRUCTURE FOR SAFETY HYPODERMIC SYRINGE

BACKGROUND OF THE INVENTION

1. Field of the Invention

The present invention relates to a safety hypodermic syringe and, more particularly, to a needle holder positioning structure for safety hypodermic syringe.

2. Description of Related Art

In a safety hypodermic syringe, the plunger has an arrowhead-like front tip adapted for hooking the needle holder, for enabling the needle holder and the needle cannula at the needle holder to be pulled backwards to the inside of the barrel to prevent contamination after the service of the safety hypodermic syringe. The needle holder is press-fitted into the inside of the front section of the barrel. However, when installing the needle cannula in the needle holder, the backward pressure from the needle cannula tends to force the needle holder out of position. Further, in order to prohibit the needle holder from escaping out of the barrel from the front side of the barrel, the barrel is made having a conical front end. This conical front end design prohibits the needle holder from forward movement relative to the barrel, however it facilitates backward movement of the needle holder in the barrel during installation of the needle cannula in the needle holder. In order to ensure positive positioning of the needle holder in the barrel, the friction-fit between the needle holder and the inside wall of the barrel is enhanced. However, enhancing the friction-fit between the needle holder and the inside wall of the barrel complicates the installation of the needle holder in the barrel. Further, an injection molding mold for molding needle holders or barrels for safety hypodermic syringe has multiple cavities. Because the injection environment (fluid material filling position, injection temperature, cooling speed, etc.) in each cavity is different, it is difficult to control the dimensions of the injection-molded finished products precisely. A small specification tolerance may cause the needle holder and the barrel unable to match each other perfectly.

Therefore, it is desirable to provide a needle holder positioning structure for safety hypodermic syringe that eliminates the aforesaid problems.

SUMMARY OF THE INVENTION

The main object of the present invention is to provide a needle holder positioning structure for safety hypodermic syringe, which prevents falling of the needle holder to the inside of the barrel accidentally. It is another object of the present invention to provide a needle holder positioning structure for safety hypodermic syringe, which is easy and inexpensive to manufacture.

To achieve these and other objects of the present invention, the needle holder positioning structure for safety hypodermic syringe comprises a barrel, a needle holder, and a locating ring. The barrel comprises a fluid chamber. The fluid chamber has a front small inner diameter section, a rear big inner diameter section, a shoulder connected between the front small inner diameter section and the rear big inner diameter section, and an inside flange means disposed in the rear big inner diameter section adjacent to the shoulder. The needle holder comprises a tubular center base and a sleeve coaxially formed integral with the periphery of the tubular center base. The tubular center base has a retaining portion near a rear side thereof. The sleeve has a front engagement section press-fitted into the inside of the front small inner diameter section of the fluid chamber of the barrel and a springy rear expansion section. The rear expansion section has a front side edge corresponding to a back side of the shoulder of the barrel, and a rear side edge stopped at a front side of the inside flange means of the barrel. The rear expansion section defines with the periphery of the tubular center base a backwardly extended annular coupling chamber. The locating ring has an outside wall disposed in contact with an inside wall of the rear big inner diameter section of the fluid chamber of the barrel for enabling the locating ring to be moved axially in the barrel, and an inside wall disposed in contact with the periphery of the tubular center base of the needle holder for enabling the locating ring to be moved axially relative to the needle holder. The outside wall of the locating ring has a front section forming a neck adapted for engaging into the rear expansion section of the sleeve of the needle holder. The neck has an outer diameter not less than the inner diameter of the expansion section of the sleeve of the needle holder so as to expand the rear expansion section of the sleeve for enabling the rear side edge of the rear expansion section stopped at the front side of the inside flange means of the barrel. The locating ring further comprises a first retaining portion integral with a front part of the inside wall and adapted for engaging the retaining portion of the tubular center base of the needle holder, and a second retaining portion formed integral with a rear part of the inside wall and adapted for engaging the arrowhead-like front retainer tip of a plunger to be inserted into the fluid chamber of the barrel. When the neck of the locating ring inserted into the backwardly extended annular coupling chamber of the needle holder, the rear expansion section of the sleeve is expanded and positioned in the barrel between the shoulder and the inside flange means of the barrel, and therefore the needle holder is prohibited from backward movement relative to the barrel. Because this positioning design requires less precision, the manufacturing cost of the safety hypodermic syringe is low. Further, the flange, expansion section, retaining portions can be respectively formed of a unitary flange, or multiple protruded blocks, strips, protruded means of wedge-like, triangular, or arched cross section.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
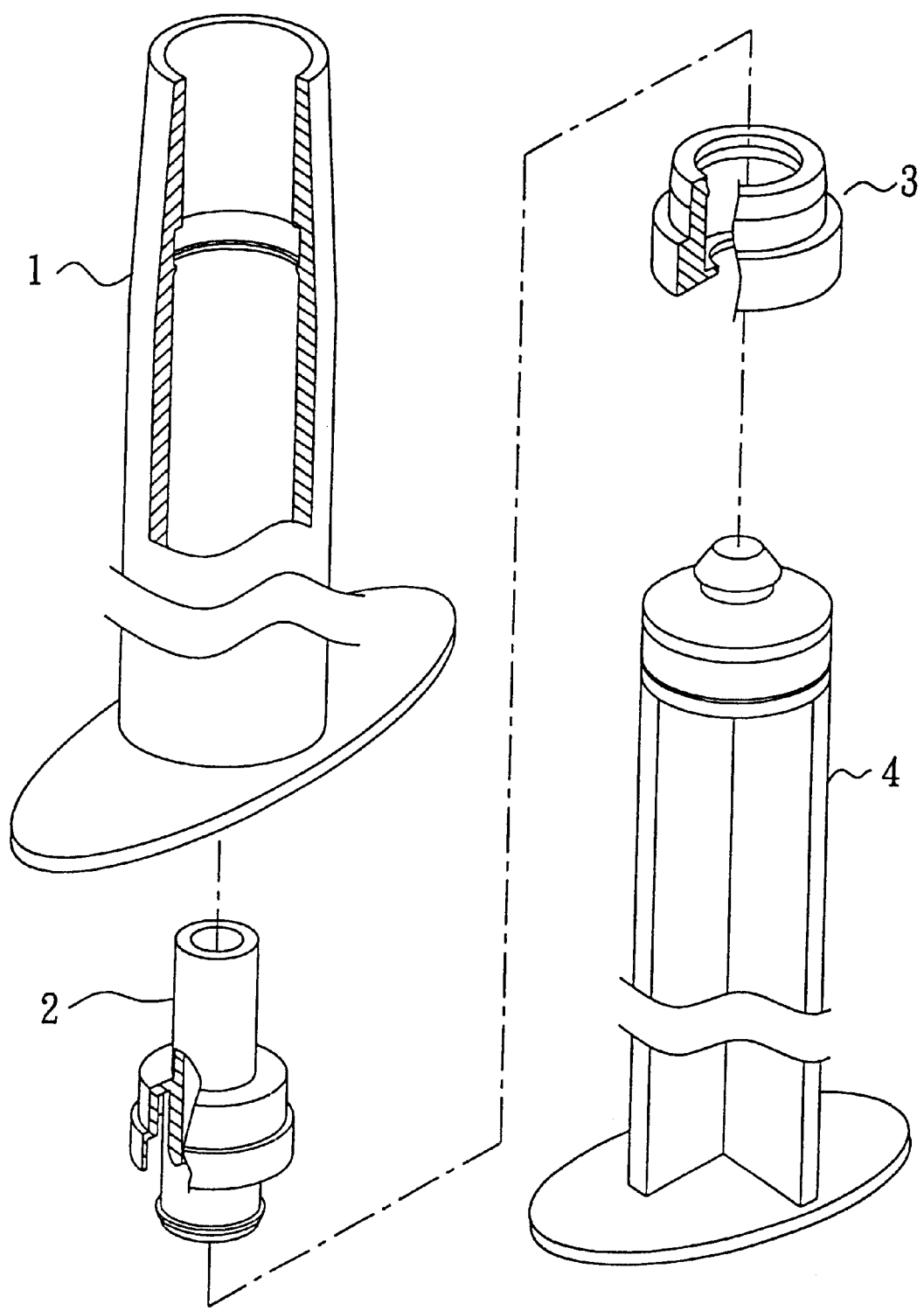
FIG. 1 is an exploded view of the preferred embodiment of the present invention.

With reference to FIG. 1, a safety hypodermic syringe is shown comprised of a barrel 1, a needle holder 2, a locating ring 3, and a plunger 4.

Figure 2:
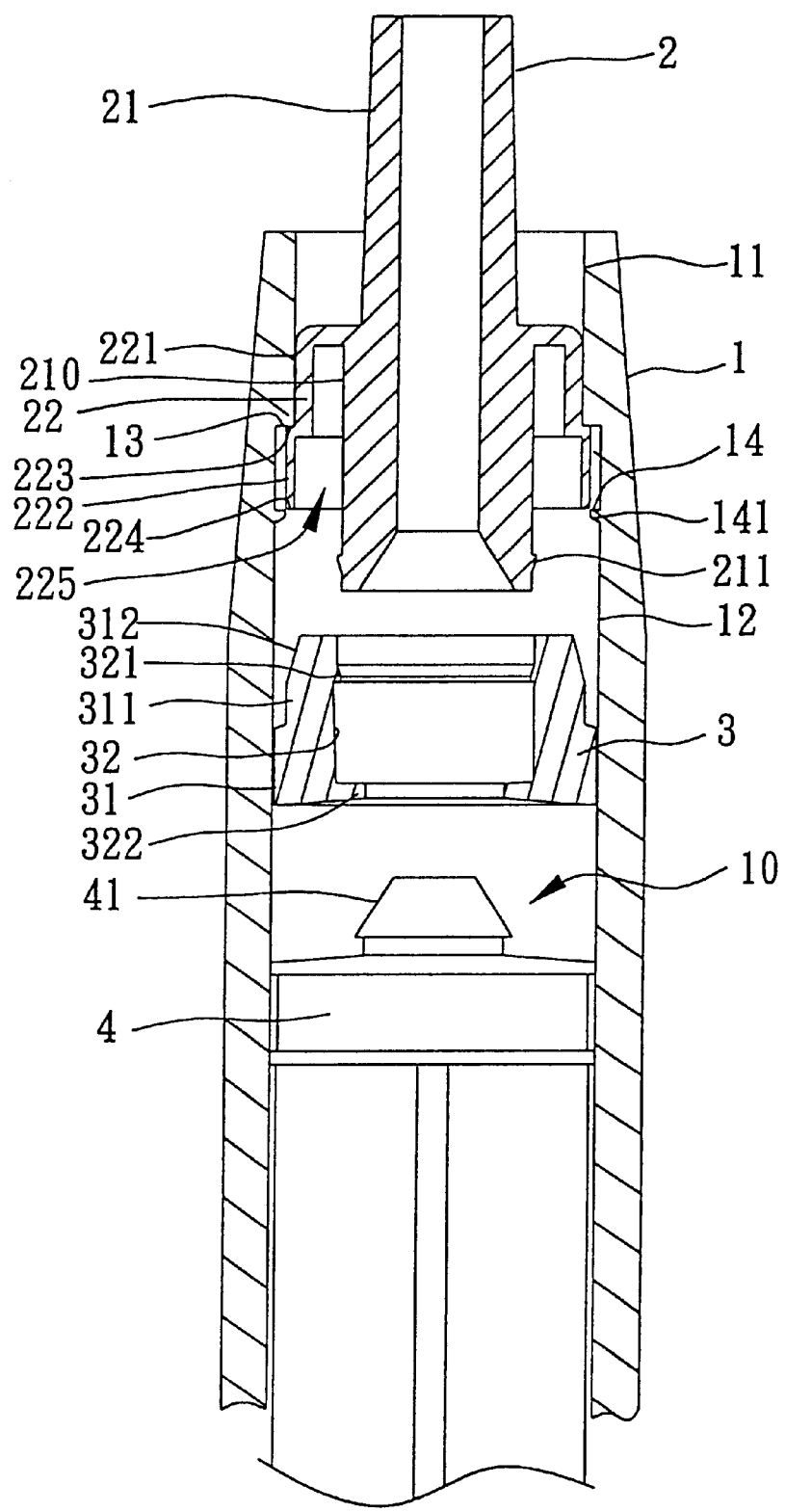
FIG. 2 is a sectional view of the preferred embodiment of the present invention before the connection of the locating ring to the needle holder.

Referring to FIG. 2, the barrel 1 is a hollow cylindrical member comprising a fluid chamber 10. The fluid chamber 10 has a front small inner diameter section 11, a rear big inner diameter section 12, a shoulder 13 connected between the front small inner diameter section 11 and the rear big inner diameter section 12, and an inside flange 14 disposed in the rear big inner diameter section 12 near the shoulder 13.

Referring to FIGS. 1 and 2 again, the needle holder 2 is adapted for holding a needle cannula (not shown) in the front side of the barrel 1, comprising a tubular center base 21, and a sleeve 22 coaxially formed integral with the periphery of the tubular center base 21. The sleeve 22 has a front engagement section 221 and a rear expansion section 222. The front engagement section 221 of the sleeve 22 is press-fitted into the inside of the front small inner diameter section 11 of the barrel 1 from the rear side. The rear expansion section 222 has a front side edge 223 corresponding to the back side of the shoulder 13 of the barrel 1, and a rear side edge 224 stopped at the front side of the inside flange 14 of the barrel 1. The rear expansion section 222 defines with the periphery 210 of the tubular center base 21 a backwardly extended annular coupling chamber 225.

Figure 3:
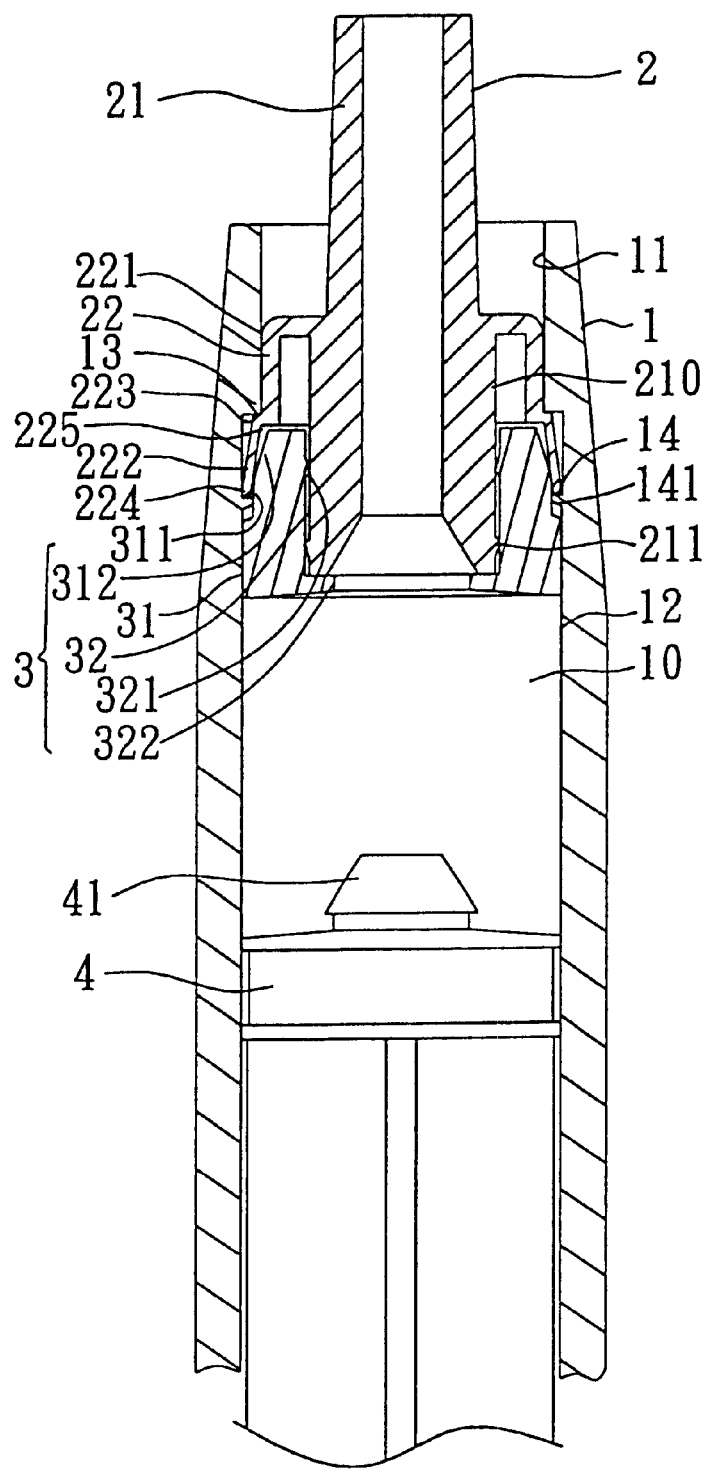
FIG. 3 is a sectional assembly view of the preferred embodiment of the present invention showing the locating ring fastened to the needle holder.

Referring to FIG. 3 and FIGS. 1 and 2 again, the locating ring 3 has an outside wall 31 and an inside wall 32. The outside wall 31 is disposed in contact with the inside wall of the rear big inner diameter section 12 of the barrel 1 for enabling the locating ring 3 to be moved axially in the barrel 1. The inside wall 32 is disposed in contact with the periphery 210 of the tubular center base 21 of the needle holder 2 for enabling the locating ring 3 to be moved axially relative to the needle holder 2. The outside wall 31 has a front section forming a neck 311. The outer diameter of the neck 311 is slightly greater than the inner diameter of the expansion section 222 of the sleeve 22 of the needle holder 2. The locating ring 3 further comprises a first retaining portion 321 integral with a front part of the inside wall 32, and a second retaining portion 322 integral with a rear part of the inside wall 32. The first retaining portion 321 is adapted for engaging a retaining portion 211 at the rear end of the periphery 210 of the tubular center base 21 of the needle holder 2. The second retaining portion 322 is adapted for engaging the arrowhead-like front retainer tip 41 of the plunger 4. According to this embodiment, the retaining portion 211 of the needle holder 2 is an outside annular flange around the periphery 210 of the tubular center base 21. The first retaining portion 321 is an annular flange extended around the inside wall 32 of the locating ring 3. The retaining portion 211 has a wedge-like cross section, and the first retaining portion 321 has an opposing wedge-like cross section. So the first retaining portion 321 can be easily forced into engagement with the retaining portion 211 and hard to be taken apart.

The assembly process of the present invention is outlined hereinafter with reference to FIG. 3. The needle holder 2 and the locating ring 3 are inserted in proper order into the fluid chamber 10 of the barrel 1 from the rear side, and then the plunger 4 is inserted into the fluid chamber 10 of the barrel 1 to push the locating ring 3 and the needle holder 2 forwards. When pushing the locating ring 3 and the needle holder 2 forwards in the fluid chamber 10 of the barrel 1, the front engagement section 221 of the sleeve 22 is forced into engagement with the front small inner diameter section 11 of the barrel 1, and the neck 311 of the locating ring 3 is engaged into the backwardly extended annular coupling chamber 225 of the needle holder 2. When engaging the neck 311 of the locating ring 3 into the backwardly extended annular coupling chamber 225 of the needle holder 2, the rear expansion section 222 is expanded outwards to force the rear side edge 224 into engagement with the front side of the inside flange 14 of the barrel 1, stopping the needle holder 2 from backward movement in the barrel 1.

As shown in FIG. 3, the neck 311 of the locating ring 3 has a front bevel face 312 adapted for guiding the neck 311 of the locating ring 3 into the backwardly extended annular coupling chamber 225 of the needle holder 2. The inside flange 14 of the barrel 1 is an inwardly protruded annular flange having a beveled rear bevel face 141 adapted for guiding the needle holder 2 into position. Alternatively, the inside flange 14 can be formed of separated protruding blocks, wedged blocks, or blocks of triangular or arched cross section equiangularly spaced around the inner surface of the rear big inner diameter section 12 of the barrel 1.

Figure 4:
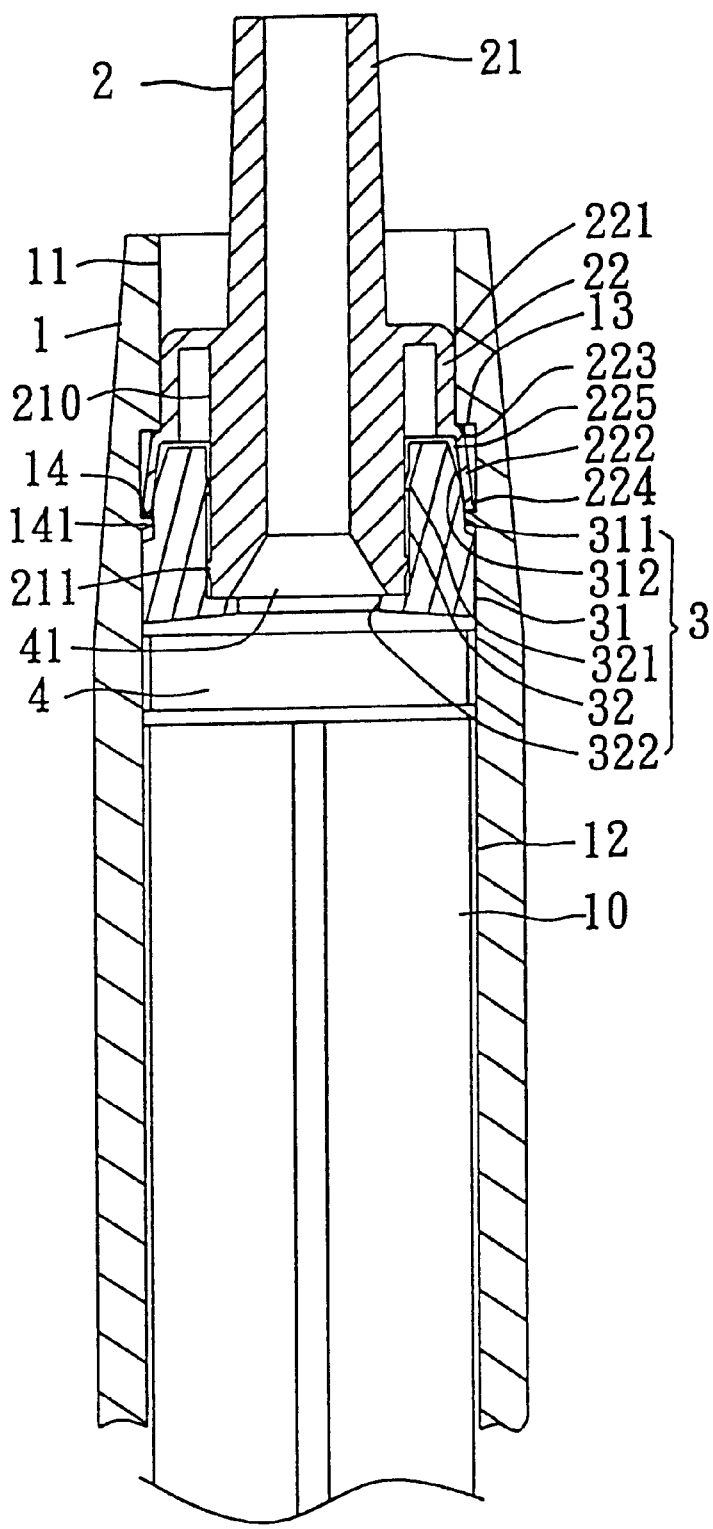
FIG. 4 is a sectional view showing the action of the preferred embodiment of the present invention (I).

Referring to FIG. 4, when pushed the plunger 4 to the front limit position (the injection action completed), a further forward pressure is applied to the plunger 4 to force the arrowhead-like front retainer tip 41 of the plunger 4 into engagement with the second retaining portion 322 of the locating ring 3.

Figure 5:
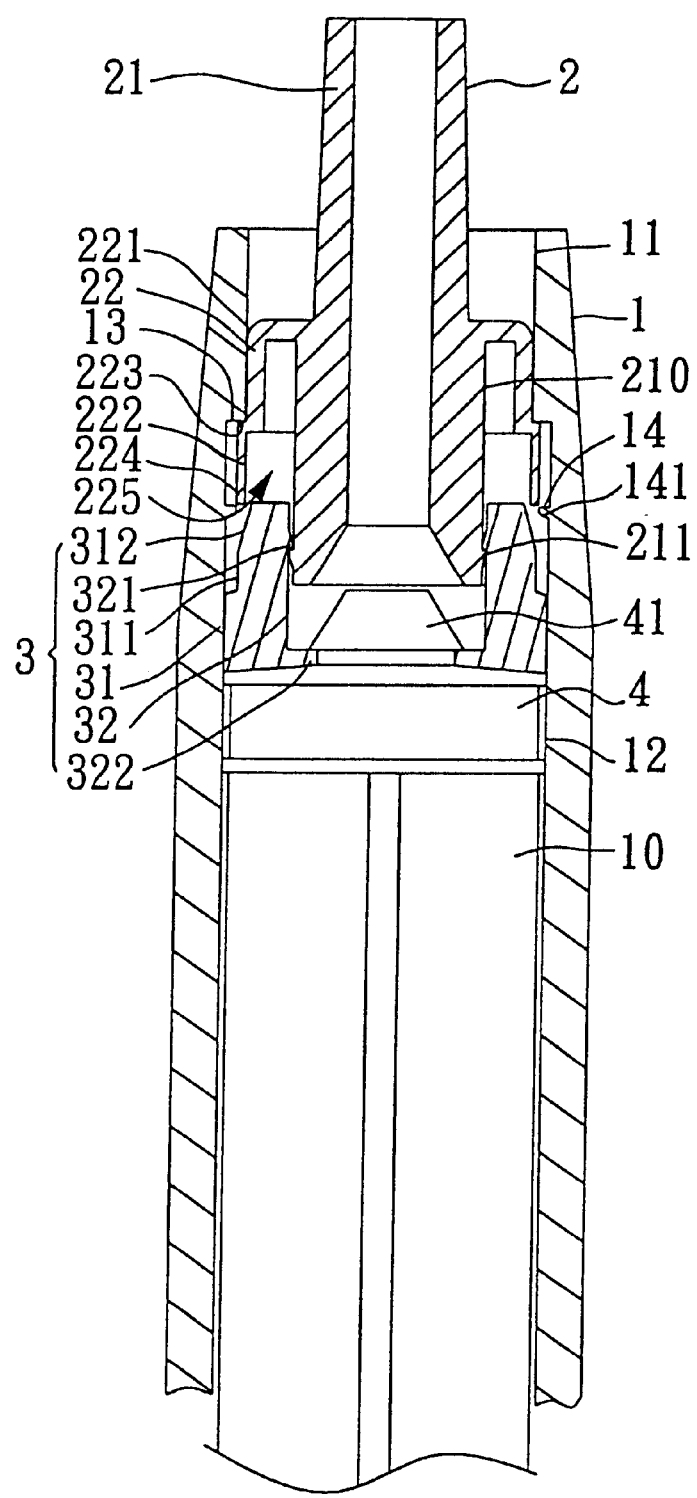
FIG. 5 is a sectional view showing the action of the preferred embodiment of the present invention (II).

Referring to FIG. 5, after engagement of the arrowhead-like front retainer tip 41 of the plunger 4 with the second retaining portion 322 of the locating ring 3, the plunger 4 is pulled backwards to move the locating ring 3 relative to the needle holder 2, thereby causing the first retaining portion 321 of the locating ring 3 to be forced into engagement with the retaining portion 211 of the tubular center base 21 of the needle holder 2, for enabling the needle holder 2 to be moved with the locating ring 3 and the plunger 4 backwards. At this time, the neck 311 of the locating ring 3 is disconnected from the expansion section 222 of the needle holder 2, and the expansion section 222 returns to its former shape and is disengaged from the inside flange 14 of the barrel 1.

Figure 6:
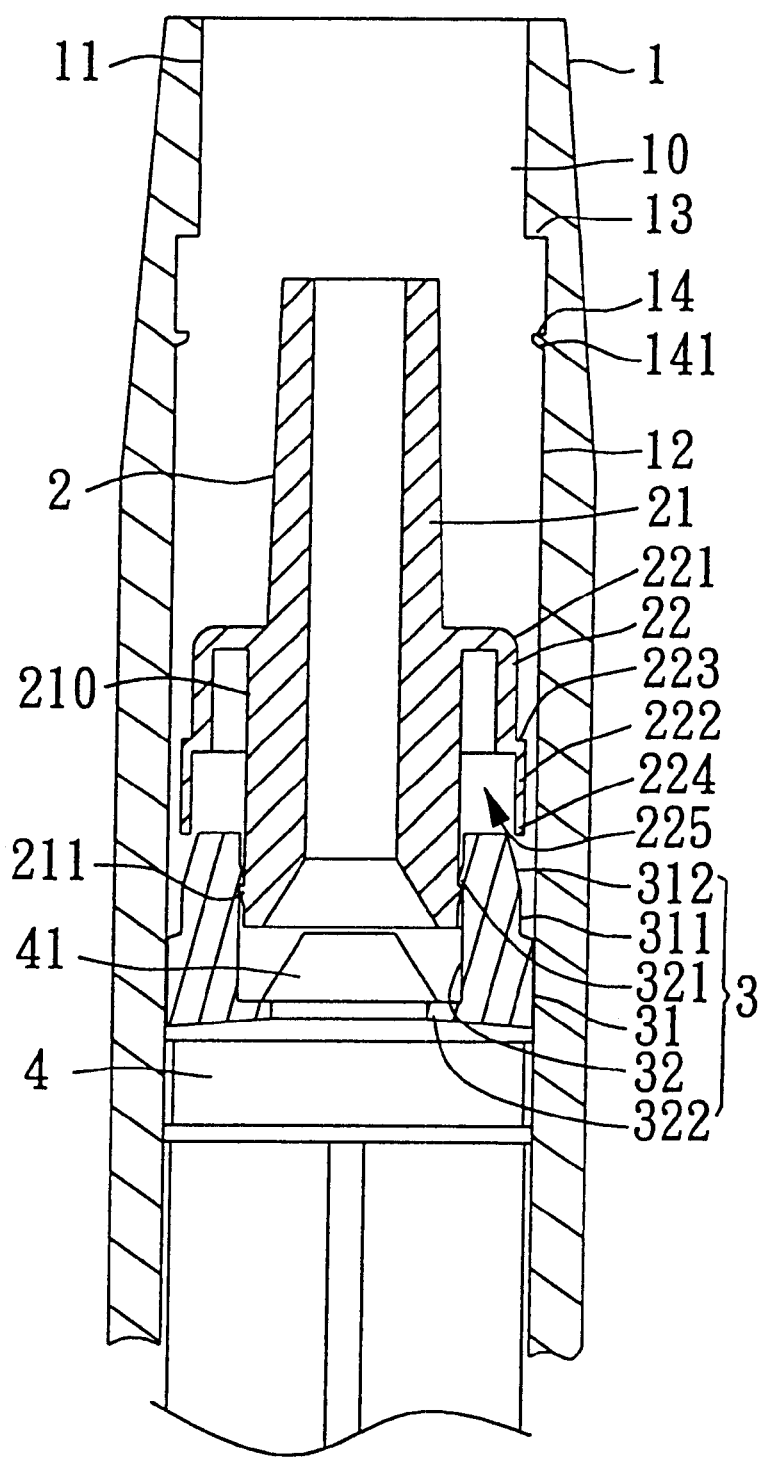
FIG. 6 is a sectional view showing the action of the preferred embodiment of the present invention (III).

Referring to FIG. 6, when continuously pulling the plunger backwards after engagement of the first retaining portion 321 of the locating ring 3 with the retaining portion 211 of the tubular center base 21 of the needle holder 2, the needle holder 2 is moved with the locating ring 3 backwards to the inside of the barrel 1.

Figure 7:
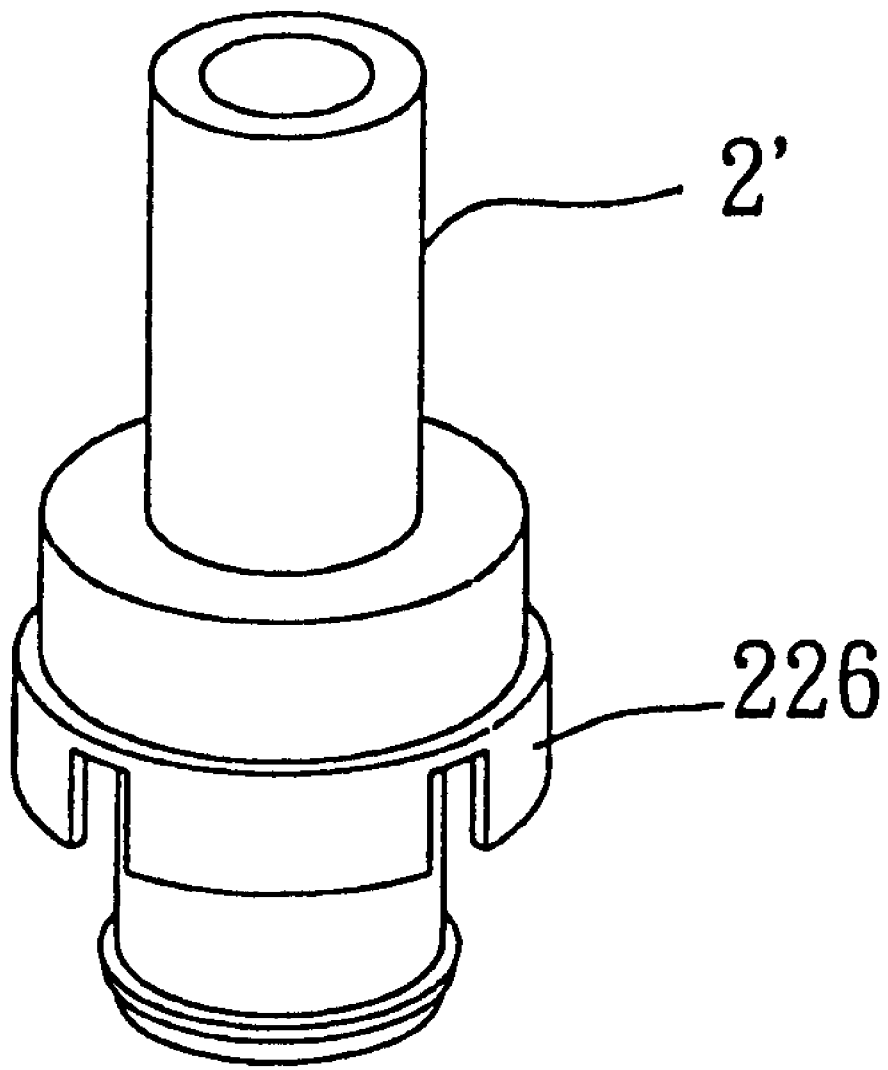
FIG. 7 is an elevational view of an alternate form of the needle holder according to the present invention.

According to the present preferred embodiment, the expansion section 222 of the needle holder 2 is an annular wall of thin thickness having a springy power. FIG. 7 shows an alternate form of the present invention. According to this alternate form, the rear expansion section of the sleeve of the needle holder 2' is comprised of four equiangularly spaced springy strips 226. The spring strips 226 are preferably molded from plastics, for example, polypropylene. Alternatively, resilient steel or any of a variety of springy materials may be used for the spring strips 226 or the aforesaid rear expansion section 222.

According to the present invention, the precision requirement for the needle holder and the barrel is less critical; therefore the needle holder and the barrel can be made by injection molding to reduce the manufacturing cost and increase the yielding rate.

A prototype of needle holder positioning structure for safety hypodermic syringe has been constructed with the features of FIGS. 1~7. The safety hypodermic syringe functions smoothly to provide all of the features discussed earlier.

Although a particular embodiment of the invention has been described in detail for purposes of illustration, various modifications and enhancements may be made without departing from the spirit and scope of the invention.

Accordingly, the invention is not to be limited except as by the appended claims.

What is claimed is:

1. A needle holder positioning structure for safety hypodermic syringe comprising:

a barrel, said barrel comprising a fluid chamber, said fluid chamber having a front small inner diameter section, a rear big inner diameter section, a shoulder connected between said front small inner diameter section and said rear big inner diameter section, and an inside flange means disposed in said rear big inner diameter section adjacent to said shoulder;

a needle holder mounted in said barrel, said needle holder comprising a tubular center base and a sleeve coaxially formed integral with the periphery of said tubular center base, said tubular center base having a retaining portion near a rear side thereof, said sleeve having a front engagement section press-fitted into the inside of the front small inner diameter section of the fluid chamber of said barrel and a springy rear expansion section, said rear expansion section having a front side edge corresponding to a back side of said shoulder of said barrel and a rear side edge stopped at a front side of the inside flange means of said barrel, said rear expansion section defining with the periphery of said tubular center base a backwardly extended annular coupling chamber; and a locating ring mounted inside said barrel and coupled to said needle holder, said locating ring having an outside wall disposed in contact with an inside wall of the rear big inner diameter section of said fluid chamber of said barrel for enabling said locating ring to be moved axially in said barrel, an inside wall disposed in contact with the periphery of said tubular center base of said needle holder for enabling said locating ring to be moved axially relative to said needle holder, the outside wall of said locating ring having a front section forming a neck adapted for engaging into said rear expansion section of said sleeve of said needle holder, said neck having an outer diameter not less than the inner diameter of said expansion section of said sleeve of said needle holder so as to expand said rear expansion section of said sleeve for enabling the rear side edge of the rear expansion section stopped at the front side of the inside flange means of said barrel, a first retaining portion integral with a front part of the inside wall of said locating ring and adapted for engaging the retaining portion of said tubular center base of said needle holder, and a second retaining portion formed integral with a rear part of the inside wall of said locating ring.

2. The needle holder positioning structure for safety hypodermic syringe as claimed in claim 1, wherein the inside flange means of said barrel is an inwardly protruded inside annular flange.

3. The needle holder positioning structure for safety hypodermic syringe as claimed in claim 1, wherein the inside flange means of said barrel has a wedge-like cross section.

4. The needle holder positioning structure for safety hypodermic syringe as claimed in claim 1, wherein the rear expansion section of said needle holder is a springy annular wall of thin thickness.

5. The needle holder positioning structure for safety hypodermic syringe as claimed in claim 1, wherein the rear expansion section of said needle holder is comprised of at least two springy strips.

6. The needle holder positioning structure for safety hypodermic syringe as claimed in claim 5, wherein the at least two springy strips of said rear expansion section of said needle holder are arranged in symmetry.

7. The needle holder positioning structure for safety hypodermic syringe as claimed in claim 1, wherein the rear expansion section of said needle holder is made from springy plastic material.

8. The needle holder positioning structure for safety hypodermic syringe as claimed in claim 1 wherein the retaining portion of said needle holder is an outside annular flange extended around the periphery of said tubular center base.

9. The needle holder positioning structure for safety hypodermic syringe as claimed in claim 1, wherein the neck of said locating ring has a front bevel face adapted for guiding the neck of said locating ring into the backwardly extended annular coupling chamber of said needle holder.

10. The needle holder positioning structure for safety hypodermic syringe as claimed in claim 1, wherein the first retaining portion of said locating ring is an inside annular flange extended around the inside wall of said locating ring.

* * * * *